(12) United States Patent
Kim et al.

(10) Patent No.: US 7,179,908 B2
(45) Date of Patent: Feb. 20, 2007

(54) WATER-AND ORGANIC-SOLUBLE CUCURBITURIL DERIVATIVES, THEIR PREPARATION METHODS, THEIR SEPARATION METHODS AND USES

(75) Inventors: Kimoon Kim, Pohang (KR); Jianzhang Zhao, Pohang (KR); Hee-Joon Kim, Pohang (KR); Soo-Young Kim, Pohang (KR); Jinho Oh, Pohang (KR)

(73) Assignee: Pohang University of Science and Technology Foundation, Pohang-shi (KR)

( * ) Notice: Subject to any disclaimer, the term of this patent is extended or adjusted under 35 U.S.C. 154(b) by 0 days.

(21) Appl. No.: 10/363,468

(22) PCT Filed: Jul. 3, 2002

(86) PCT No.: PCT/KR02/01259

§ 371 (c)(1),
(2), (4) Date: Mar. 4, 2003

(87) PCT Pub. No.: WO03/004500

PCT Pub. Date: Jan. 16, 2003

(65) Prior Publication Data

US 2003/0212268 A1    Nov. 13, 2003

(30) Foreign Application Priority Data

Jul. 4, 2001 (KR) .................. 2001-39756

(51) Int. Cl.
*C07D 487/22* (2006.01)
(52) U.S. Cl. ....................... 540/460
(58) Field of Classification Search ......... 540/460
See application file for complete search history.

(56) References Cited

U.S. PATENT DOCUMENTS

| 6,365,734 B1 | 4/2002 | Kim et al. |
| 2002/0133003 A1 | 9/2002 | Kim et al. |

FOREIGN PATENT DOCUMENTS

| DE | 19603377 A1 | 8/1997 |
| EP | 1094065 A2 * | 4/2001 |
| JP | 57154185 A2 | 9/1982 |
| WO | WO 00/68232 | 11/2000 |

OTHER PUBLICATIONS

Beilstein Records (BRN) 5544184, 1987.*
Zhao et al., Angewandte Chemie-International Edition, Nov. 2001, 40(22), pp. 4233-4235.*
Polozov. G. I. et al., *Vestsi Akademii Navuk BSSR, Seryya Khimichnykh Navuk*, (3), 62-9, (1978) (English language Abstract).
Kavtaradze, N. N. et al, *Zhurnal Fizicheskoi Khimii*, 38(4), 1004-5 (1964) (English language Abstract).

* cited by examiner

Primary Examiner—Laura L. Stockton
(74) Attorney, Agent, or Firm—Leydig, Voit & Mayer

(57) ABSTRACT

Provided are cucurbituril derivatives having the formula (1), their preparation methods and uses:

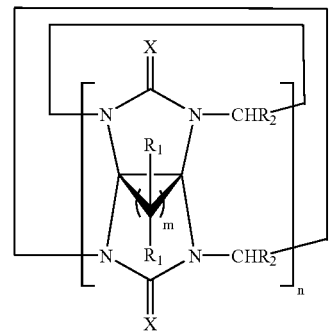

where X is O, S or NH; $R_1$ and $R_2$ are each independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n and m are independently integers from 4 to 20 and from 1 to 7, respectively. The cucurbituril derivative has enhanced solubility in common solvents, thereby providing wider applications.

10 Claims, 2 Drawing Sheets

WATER- AND ORGANIC-SOLUBLE CUCURBITURIL DERIVATIVES, THEIR PREPARATION METHODS, THEIR SEPARATION METHODS AND USES

BACKGROUND OF THE INVENTION

1. Field of the Invention

The present invention relates to water- and organic-soluble cucurbituril derivatives, their preparation methods, their separation methods and uses, and more particularly, to novel cucurbituril derivatives having various repeating units and internal cavities of various sizes and being soluble in pure water at a neutral pH or in common organic solvents, their preparation methods, methods of separating pure cucurbituril derivatives, and their uses.

2. Description of the Related Art

Cucurbituril is a compound whose preparation was first reported by Behrend et al. in 1905 (*Liebigs Ann. Chem.* 1905, 339, 1). According to their report, the condensation of glycoluril and excess formaldehyde in the presence of hydrochloric acid (HCl) produces an amorphous solid. Dissolution of the solid in hot concentrated sulfuric acid, dilution of the solution with water followed by slow cooling of the solution to room temperature produces a crystalline material. They wrongly characterized this substance as $C_{10}H_{11}N_7O_4 \cdot 2H_2O$, whose structure was, however, not yet identified.

In 1981, this substance was rediscovered by Mock and coworkers. They correctly characterized it as a hexameric macrocyclic compound with composition of $C_{36}H_{36}N_{24}O_{12}$, which was also confirmed by X-ray crystal structure determination (*J. Am. Chem. Soc.*, 1981, 103, 7367). They named it cucurbituril which we from now on refer to as cucurbit[6]uril. Since then an improved preparation procedure for cucurbit[6]uril has been disclosed (DE 196 03 377 A1).

In 2000, the conventional preparation method of cucurbit[6]uril was improved by Kimoon Kim and coworkers to synthesize and separate cucurbit[6]uril and its homologue cucurbitu[n]uril (n=5, 7 and 8), which was confirmed by X-ray crystal structure determination (*J. Am. Chem. Soc.*, 2000, 122, 540).

The above-described cucurbituril derivatives are compounds of unsubstituted glycoluril monomers and are disadvantageously soluble only in an aqueous acidic solution.

As a cucurbituril derivative with a substituent other than hydrogen, decamethylcucurbit[5]uril, in which five dimethanodimethylglycoluril units form a cyclic structure by the condensation of dimethylglycoluril and formaldehyde, has only been reported (*Angew. Chem. Int. Ed. Engl.* 1992, 31, 1475). However, this compound is also soluble only in an aqueous acidic solution.

As described above, the cucurbituril derivatives that have been prepared and known up to now are very limited in terms of their applications because they are insoluble in pure water at a neutral pH or common organic solvents such as methanol.

International Patent Publication WO 00/68232 discloses cucurbit[n]uril having the following formula:

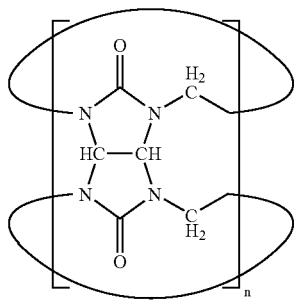

where n is a value of 4 to 12.

In addition, WO 00/68232 discloses substituted glycoluril derivatives having the following formulas:

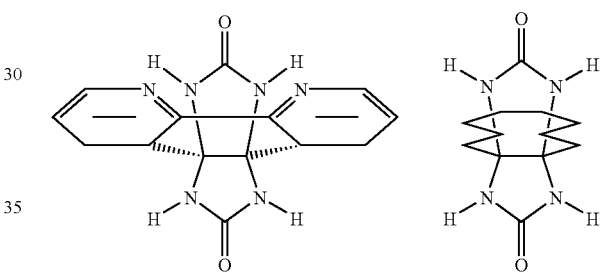

However, cucurbituril derivatives prepared from the above-described glycoluril derivatives are not disclosed in the cited reference. Also, since the glycoluril derivatives have considerably large substituents, it is quite difficult to synthesize cucurbituril derivatives corresponding thereto due to steric hindrance.

SUMMARY OF THE INVENTION

To solve the above-described problems, the first objective of the present invention is to provide novel cucurbituril derivatives having various sized cavities and/or having enhanced solubilities in common solvents, and novel glycoluril derivatives used in preparing the cucurbituril derivatives.

The second objective of the present invention is to provide methods of preparing the cucurbituril derivatives and the glycoluril derivatives.

The third objective of the present invention is to provide methods of separating pure cucurbituril derivatives from a mixture of the cucurbituril derivatives.

The fourth objective of the present invention is to provide the uses of the cucurbituril derivatives.

The first objective of the present invention is achieved by cucurbituril derivatives having the formula (1):

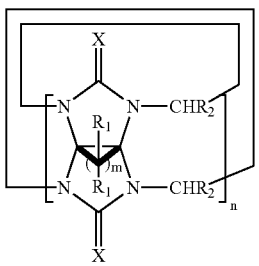

where X is O, S or NH; $R_1$, and $R_2$ are each independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n and m are independently integers from 4 to 20 and from 1 to 7, respectively.

According to another aspect of the present invention, there is provided a glycoluril derivative having the formula (2):

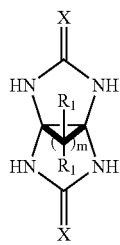

where X is O, S or NH; $R_1$ is independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and m is an integer from 1 to 7, exclusive of 4.

The second objective of the present invention is achieved by a method for preparing a cucurbituril derivative having the formula (1), including (a-2) mixing and stirring a compound having the formula (2) and an aldehyde compound having the formula (A), and (b-2) adding acid to the reaction mixture and stirring to complete the reaction,

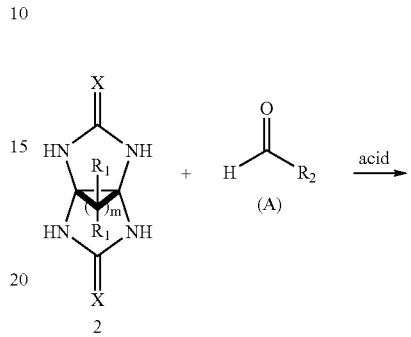

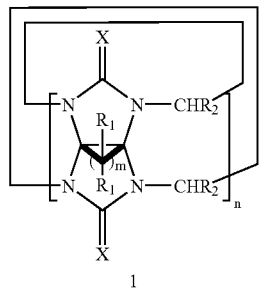

where X is O, S or NH; $R_1$ and $R_2$ are each independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n and m are independently integers from 4 to 20 and from 1 to 7, respectively.

In step (a-2), the acid is preferably added in an amount of 3 to 7 moles and the aldehyde compound having the formula (A) is preferably added in an amount of 2 to 20 moles with respect to 1 mole of the compound having the formula (2), and the reaction temperature is preferably in the range of 50 to 150° C. Also, in step (b-2), the reaction temperature is preferably in the range of 50 to 150° C.

Among reaction products of step (b-2), the cucurbituril derivative with n=5 is preferably produced in a yield of 15 to 50%, the cucurbituril derivative with n=6 is preferably produced in a yield of 2 to 10%, and the cucurbituril derivatives with n=4 and 7 to 20 are preferably produced in a yield of 1 to 5%, respectively.

According to another aspect of the present invention, there is provided a method for preparing a glycoluril derivative having the formula (2):

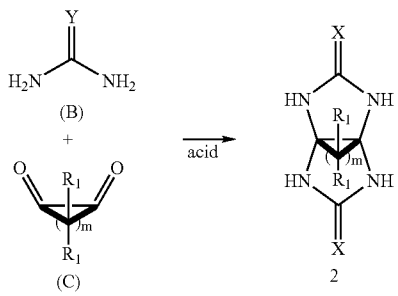

where X is O, S or NH; $R_1$ and $R_2$ are each independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and m is an integer from 1 to 7, exclusive of 4, the method including (a-1) adding an aqueous acidic solution or an acid-containing organic solvent to a mixture of a urea derivative (B) and a cyclodione compound (C) for reaction, and (b-1) removing water or the organic solvent from the reaction mixture.

In step (a-1), the reaction temperature is preferably in the range of 70 to 120° C. Preferably, the amount of the cyclodione compound (C) used in the reaction is 0.1 to 0.5 moles for each mole of the urea derivative (B). Also, the aqueous acidic solution is preferably selected from the group consisting of trifluoroacetic acid, methane sulfonic acid, acetic acid, hydrochloric acid, nitric acid and sulfuric acid, and the acid-containing organic solvent is selected from the group consisting of benzene and toluene.

To accomplish the third objective, the present invention provides a method of separating the cucurbituril derivative having the formula (1) from the cucurbituril derivative mixture by a fractional crystallization. The fractional crystallization procedure is based on different solubilities in at least one solvent selected from the group consisting of water, acetone and acetonitrile.

The fourth objective of the present invention is achieved by a method for using the cucurbituril derivative to remove organic dyes from waste water, heavy metal from water, and radioactive isotopes from radioactive wastes, to capture and remove unpleasant odor, and air pollutants, and to deodorize and decolorize livestock waste water and ironwork waste water. Alternatively, the present invention can be used for sensors for sensing ammonium ions, organic amines, amino acid derivatives, nucleic acid bases, alkali metal or alkaline earth metal ions, additives to polymers, cosmetics, artificially scented papers or textiles, pesticides and herbicides, drugs, and drug carriers. Further, the present invention can be used for extraction and purification of fullerene or caborane compounds, and used as packing materials of chromatographic columns, as additives to gas separation membranes, as catalysts for various chemical reactions. In particular, in a preferred embodiment of the present invention, there is provided an ion sensor employing the cucurbituril derivative as an ion selective material.

The cucurbituril derivatives according to the present invention are represented by the formula (1):

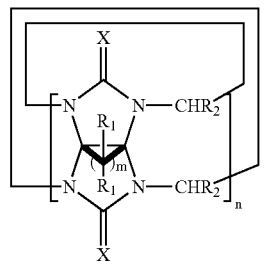

where X is O, S or NH; $R_1$ and $R_2$ are independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and n and m are independently integers from 4 to 20 and from 1 to 7, respectively.

The alkyl groups of 1 to 30 carbon atoms for $R_1$ and $R_2$ may include methyl, ethyl, propyl, isopropyl and t-butyl groups. The alkenyl groups of 1 to 30 carbon atoms for $R_1$ and $R_2$ may include propylene and butene groups, and the alkynyl groups of 1 to 30 carbon atoms therefore may include a hexynyl group. The alkylthio groups of 1 to 30 carbon atoms may include butylmethylsulfide and octanethiol groups. The alkylcarboxyl groups of 1 to 30 carbon atoms may include carboxypropyl and carboxylbutyl groups. The hydroxylalkyl groups of 1 to 30 carbon atoms may include hydroxybutyl and hydroxyethyl groups. The alkylsilyl groups of 1 to 30 carbon atoms may include aryltriethylsilyl and vinyltriethylsilyl groups, and the alkoxy groups of 1 to 30 carbon atoms may include methoxy and ethoxy groups. The haloalkyl groups of 1 to 30 carbon atoms may include $CF_3$ and $CH_2Cl$, the alkylamine groups of 1 to 30 carbon atoms may include methylamine and ethylamine groups, and the aminoalkyl groups of 1 to 30 carbon atoms may include 2-aminobutyl and 1-aminobutyl groups. The unsubstituted cycloalkyl groups of 5 to 30 carbon atoms may include cyclohexyl and cyclopentyl groups, and the cycloalkyl groups of 4 to 30 carbon atoms with hetero atoms may include piperidyl and tetrahydrofuranyl groups. The unsubstituted aryl groups of 6 to 30 carbon atoms may include phenyl, benzyl and naphthyl groups, and the aryl groups of 6 to 30 carbon atoms with hetero atoms may include pentafluorophenyl and pyridyl groups.

In consideration of the above examples of $R_1$ and $R_2$ in the formula (1) hereinabove, the following compounds may be examples of the cucurbituril derivatives having the formula (1).

In other words, in the formula (1) hereinabove, $R_1$ may be hydrogen, methyl, ethyl, propyl, isopropyl, butyl, isobutyl, t-butyl, phenyl or pyridyl group, and $R_2$ may be hydrogen, methyl, propyl, phenyl, trichloromethyl, trifluoromethyl, parafluorophenyl or α, α, α-trifluorotolyl group. Alternatively, $R_1$ may be hydrogen, and $R_2$ may be hydrogen, methyl, ethyl, propyl, phenyl, trichloromethyl, trifluoromethyl, parafluorophenyl or α, α, α-trifluorotolyl group. In another embodiment, $R_1$ may be methyl group, and $R_2$ may be hydrogen, methyl, ethyl, propyl, phenyl, trichloromethyl, trifluoromethyl, parafluorophenyl or α, α, α-trifluorotolyl group. More preferable cucurbituril derivatives have the formula (1) hereinabove, wherein X=O, $R_1$ and $R_2$ are both hydrogens, n is a value of 4 to 20 and m is a value of 1 to 7, and wherein X=NH or S, $R_1$ and $R_2$ are both hydrogens, n is a value of 4 to 20 and m is a value of 1 to 7.

In particular, the cucurbituril derivatives according to the present invention wherein n=5, m=4, X=O and $R_1$ and $R_2$ are both hydrogens, have high solubilities, that is, $1 \times 10^{-1}$ to $3 \times 10^{-1}$ M in water, and $1 \times 10^{-4}$ to $1 \times 10^{-2}$ M in an organic solve selected from the group consisting of methanol, ethanol, dimethylsulfoxide, dimethylformamide and acetonitrile. As described above, the cucurbituril derivatives according to the present invention are soluble in common solvents, thereby providing wider applications.

Alternatively, the present invention provides glycoluril derivatives having the formula (2), and is used for preparing a cucurbituril derivative having the formula (1):

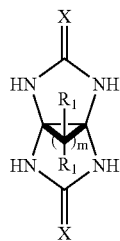

where X is O, S or NH; $R_1$ is independently selected from the group consisting of hydrogen, alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, nitro group, alkylamine groups of 1 to 30 carbon atoms, amine group, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms; and m is an integer from 1 to 7, exclusive of 4.

In $R_1$ of the formula 2, the alkyl groups of 1 to 30 carbon atoms, alkenyl groups of 1 to 30 carbon atoms, alkynyl groups of 1 to 30 carbon atoms, alkylthio groups of 1 to 30 carbon atoms, alkylcarboxyl groups of 1 to 30 carbon atoms, hydroxyalkyl groups of 1 to 30 carbon atoms, alkylsilyl groups of 1 to 30 carbon atoms, alkoxy groups of 1 to 30 carbon atoms, haloalkyl groups of 1 to 30 carbon atoms, alkylamine groups of 1 to 30 carbon atoms, aminoalkyl groups of 1 to 30 carbon atoms, unsubstituted cycloalkyl groups of 5 to 30 carbon atoms, cycloalkyl groups of 4 to 30 carbon atoms with hetero atoms, unsubstituted aryl groups of 6 to 30 carbon atoms, and aryl groups of 6 to 30 carbon atoms with hetero atoms, are exemplified as defined above. More preferably, the cucurbituril derivatives have the formula (2) hereinabove, wherein m=3 or 4, $R_1$ and $R_2$ are both hydrogens.

Hereinafter, the methods for synthesizing the cucurbituril derivatives having the formula (1) according to the present invention will be described, as represented by the reaction schemes (1) and (2).

An acid is added to the glycoluril derivative having the formula (2) in an amount of 3 to 7 moles with respect to 1 mole thereof, and mixed. Preferably, the acid is diluted with water or an organic solvent to be 1 to 12M, more preferably to be 6 to 12M. Any acid capable of dissolving the glycoluril derivative having the formula (2), for example, can be used, and usable acids include hydrochloric acid, sulfuric acid, phosphoric acid, acetic acid, nitric acid and an mixtures of these acids. The organic solvent as an acid diluent may be dimethylsulfoxide, N,N-dimethylformamide, methanol, ethanol, chloroform or an mixture of these solvents.

The compound having the formula (2) (X=O) can be synthesized by the following method.

A urea derivative (B) (Y=O), that is, urea, and a cyclodione compound (C) (m=1–7) are dissolved in an aqueous acidic solution or an acid-containing organic solvent, and stirred for a certain period of time. In this step, the reaction temperature is preferably in the range of 70 to 120° C. Failure to fall within the above range is disadvantageous from the viewpoint of reactivity. The content of the cyclodione compound (C) is preferably in the range of 0.1 to 0.5 mole with respect to 1 mole of the urea derivative (B).

The aqueous acidic solution is obtained from acid selected from the group consisting of trifluoroacetic acid, methane sulfonic acid, acetic acid, hydrochloric acid, nitric acid and sulfuric acid. The acid-containing organic solvent is selected from the group consisting of benzene and toluene.

Removal of water or the organic solvent from the reaction mixture produces the compound having the formula (2) (X=O). The compound having the formula (2) with X=S or NH can be obtained by a similar procedure.

[Reaction scheme 1]

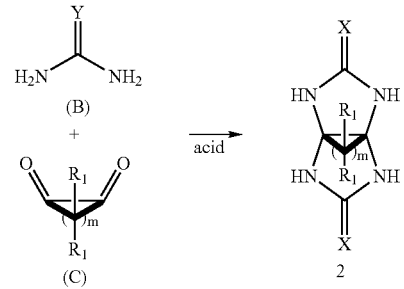

where m and $R_1$ are as defined above.

Next, as shown in the reaction scheme 2, an aldehyde compound A is added to the reaction mixture of the compound having the formula (2) (X=O) and an acid and reacted while stirring at 50 to 150° C. for 30 minutes to 1 hour. If the reaction temperature is lower than 50° C., little reaction is occurred. If the reaction temperature is beyond 150° C., decomposition of a viscous intermediate reaction product may undesirably occur.

The amount of the aldehyde compound (A) used in the reaction is 2 to 20 moles for each mole of the compound having the formula 2, preferably 4 moles. Detailed examples of the aldehyde compound (A) include formaldehyde, acetaldehyde, propionaldehyde, benzaldehyde, and the like.

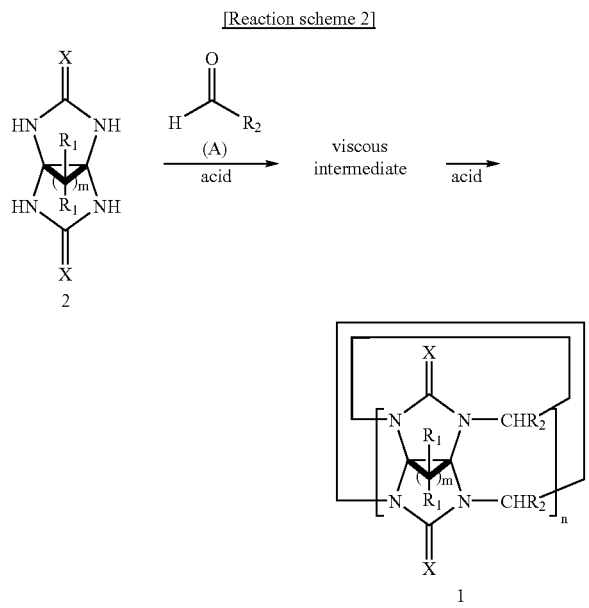

wherein m, n, $R_1$ and $R_2$ are as defined above.

During the reaction, the color of the reaction solution changes into dark red and the viscosity thereof increases, with time.

Excess acid is further added to the reaction mixture, followed by further reacting at 50 to 150° C. for 24 hours, completing the reaction. After addition of excess acid, if the reaction temperature is lower than 50° C., little reaction is occurred. If the reaction temperature is beyond 150° C., decomposition of a viscous intermediate reaction product may undesirably occur.

The final reaction product varies depending on the reaction temperature and the amount of reactants. The final reaction product is a mixture of two or more cucurbituril derivatives described above, where n is a value from 4 to 20, irrespective of m.

Typically, the reaction product is a mixture of the cucurbituril derivatives where n=4 to, 20 and m=1 to 7. Here, the cucurbituril derivative with n=5 is produced in a yield of 15 to 50%, the cucurbituril derivative with n=6 is produced in a yield of 2 to 10%, and the cucurbituril derivatives with n=4 and 7 to 20 are produced in a yield of 1 to 5%.

Then, the resulting cucurbituril derivatives are separated from each other by a fractional crystallization procedure. The separation step using the fractional crystallization procedure is based on different solubilities in solvents of water, acetone, acetonitrile and so on.

A method of synthesizing the cucurbituril derivatives having the formula (1) with X=S will now be described. The cucurbituril derivatives having the formula (1) with X=S can also be synthesized by the above-described methods using the compound having the formula (2) with X=S, instead of with X=O. Here, the compound having the formula (2) with X=S can be synthesized in the same way described previously, except that thiourea instead of urea is used. Furthermore, the above-described methods can be applied in synthesizing the cucurbituril derivatives with X=NH.

As described above, the present invention provides easy preparation methods for the cucurbituril derivatives having the formula (1), where n ranges from 5 to 20, and desired cucurbituril derivatives can be obtained in pure types using different solubilities in a common solvent. Also, according to the present invention, mixtures of two or more cucurbituril derivatives selected from the cucurbituril derivatives having the formula (1), where n ranges from 4 to 20, can be easily obtained.

The cucurbituril derivatives having the formula (1) disclosed by the present invention, which can be used as a substitute for cyclodextrin, have cavities having a diameter of 4 to 15 Å, which are able to include guest molecules, such as cyclic benzene derivatives, naphthalene derivatives, carborane derivatives, fullerene derivatives, ferrocene derivatives and adamantane derivatives in their cavities.

As described above, the cucurbituril derivatives having the formula (1) can encapsulate various compounds with different sizes, and have Lewis base atoms near the cavities of the molecule, which can interact with charged metal ions, organometallic ions or organic compounds, and thus the cucurbituril derivatives can have a wide range of applications. In particular, the cucurbituril derivatives having the formula (1) according to the present invention can be used to remove organic dyes from waste water, heavy metal from water, and radioactive isotopes from radioactive wastes, to capture and remove unpleasant odor, and air pollutants such as carbon monoxide, carbon dioxide, $NO_x$ and $SO_x$, and to deodorize and decolorize livestock waste water and ironwork waste water. Also, the cucurbituril derivatives having the formula (1) are applicable in manufacturing sensors for sensing ammonium ions, organic amines, amino acid derivatives, nucleic acid bases, alkali metal or alkaline earth metal ions. The cucurbituril derivatives having the formula (1) can be used as additives to polymers, cosmetics, artificially scented papers or textiles, pesticides and herbicides, and drugs, and used as drug carriers. The cucurbituril derivatives having the formula (1) can be used for extraction and purification of fullerene or caborane compounds, and used as packing materials of chromatographic columns, as additives to gas separation membranes, as catalysts for various chemical reactions.

In the applications of the cucurbituril derivatives disclosed by the present invention, the types of the cucurbituril derivatives are not specially limited. That is, a certain pure cucurbituril derivative or a mixture of cucurbituril derivatives can be used. However, if the difference in effect is not great among types of the cucurbituril derivatives used, use of the mixture of cucurbituril derivatives prepared by the reaction schemes 1 and 2 is preferred in terms of cost, because it does not need additional separation process.

An ion sensor employing the cucurbituril derivatives having the formula (1) will now be described.

An ion sensor includes an ion selective membrane. The ion selective membrane is formed by dissolving an ion selective material, a polymer support and a plasticizer in a solvent to prepare a composition for forming an ion selective membrane, and removing the solvent therefrom. An ion selective electrode can be formed using the ion selective membrane. Then, an ion sensor can be manufactured using the ion selective electrode by a common method.

In the composition for forming an ion selective membrane, usable ion selective materials include the cucurbituril derivatives having the formula (1). Here, the compound may be used in the form of a mixture where n=4 to 20 and m=1 to 7. The polymer support serves to support the ion selective membrane and usable examples thereof include polyvinylchloride, polyurethane and silicon rubber. The amount of the polymer support used is preferably 1 to 180 parts by weight based on 1 part by weight of the ion selective material. Here, if the amount of the polymer support is out of the above range, the efficiency of the ion sensor is poor.

In the composition for forming an ion selective membrane, the plasticizer serves to improve layer processibility and usable examples thereof include 2-nitrophenyloctylether, dioctyl adipate and dioctyl sebacate. The amount of the plasticizer used is preferably 1 to 140 parts by weight based on 1 part by weight of the ion selective material. Here, if the amount of the plasticizer is out of the above range, the layer processibility may deteriorate.

In some case, an additive for enhancing sensitivity of the ion sensor may be further included in the composition for forming an ion selective membrane. Examples of the additive include potassium tetrakis(4-chlorophenyl)borate, sodium tetrakis[3,5-bis(1,1,1,3,3,3-hexafluoro-2-methoxy-2-propyl)-phenyl]borate and potassium tetrakis[3,5-bis(trifluoromethyl)-phenyl]borate.

The ion sensor manufactured by the above-described method is used to detect heavy metals such as lead, mercury, alkaline earth metal or alkali metal, or organic matter such as acetylcholine, ammonium ions, organic amines, amino acid, derivatives thereof or nucleic acid bases.

The cucurbituril derivatives used in the ion sensor can be of the type of a pure compound or a mixture.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

SYNTHESIS EXAMPLE 1

Preparation of the Cucurbituril Derivative Having the Formula (1) where n=5, m=4, X=O, $R_1=R_2=H$ 1.9 ml of a 30% formaldehyde aqueous solution and 2.0 g of the glycoluril derivative having the formula (2) with m=4, X=O and $R_1=H$, were mixed and 0.16 ml of 37% aqueous hydrochloric acid solution was added thereto. The reaction mixture was stirred at 80° C. for 30 minutes. Then, 5 ml of water and. 2.5 ml of sulfuric acid were added and the reaction mixture was further stirred at 80° C. for 24 hours. After the reaction was completed, the resulting solution) was cooled to room temperature and diluted with 10 ml of water. Then, 300 ml of acetone was added to the reaction mixture to form a precipitate. The obtained precipitate was filtered, washed with acetone and dissolved again in 50 ml of water. The resulting solution was neutralized with triethylamine and concentrated under a reduced pressure to afford the solid mixtures which consisted of 45% of the cucurbituril derivative with. n=5, 15% of the cucurbituril derivative with n=6, 5% of the cucurbituril derivatives with n=4 and 7 to 20, and so on). The solid mixtures was washed with 20 ml of acetonitrile and recrystallized with water or a mixture of water and acetone to give a colorless crystalline cucurtbituril derivative having the formula (1) where n=5, m=4, X=O and $R_1=R_2=H$ (to be termed "CB*[5]" hereinbelow) in 40% yield.

Figure 1:
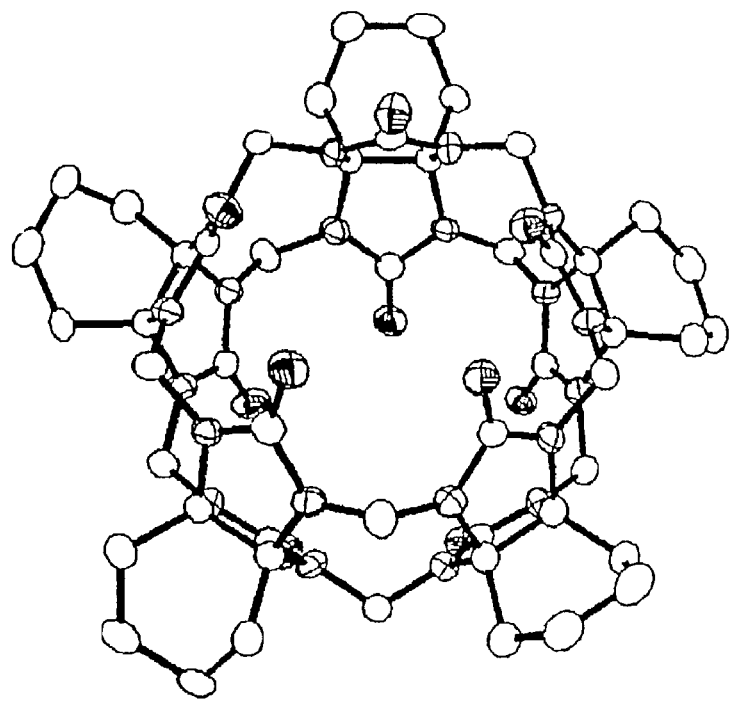
FIG. 1 is a diagram illustrating the X-ray crystal structures of cucurbituril derivatives prepared in Synthesis Example 1 of the present invention.

The crystal structure of the obtained cucurbituril derivative was determined by X-ray crystallography. The result is shown in FIG. 1. As shown in FIG. 1, it was confirmed that the cucurbituril derivative obtained in Synthesis Example 1 had internal cavities.

$^1$H NMR (300 MHz, $D_2O$): δ=5.64 (d, J=15.6 Hz, 10H), 4.33 (d, J=15.8 Hz, 10H), 2.20 (s, 20H), 1.46 (s, 20H); $^{13}$C NMR (75 MHz, $D_2O$): δ=156.33, 76.45, 43.51, 23.56, 14.0.

SYNTHESIS EXAMPLE 2

Preparation of the Cucurbituril Derivative Having the Formula (1) where n=6, m=4, X=O, $R_1=R_2=H$ The solid mixtures obtained from a solution filtered with 20 ml of acetonitrile in Synthesis Example 1 was recrystallized with water or a mixture of water and acetone to give a colorless crystalline cucurtbituril derivative having the formula (1) where n=6, m=4, X=O and $R_1=R_2=H$ (to be termed "CB*[6]" hereinbelow) in 10% yield.

Figure 2:
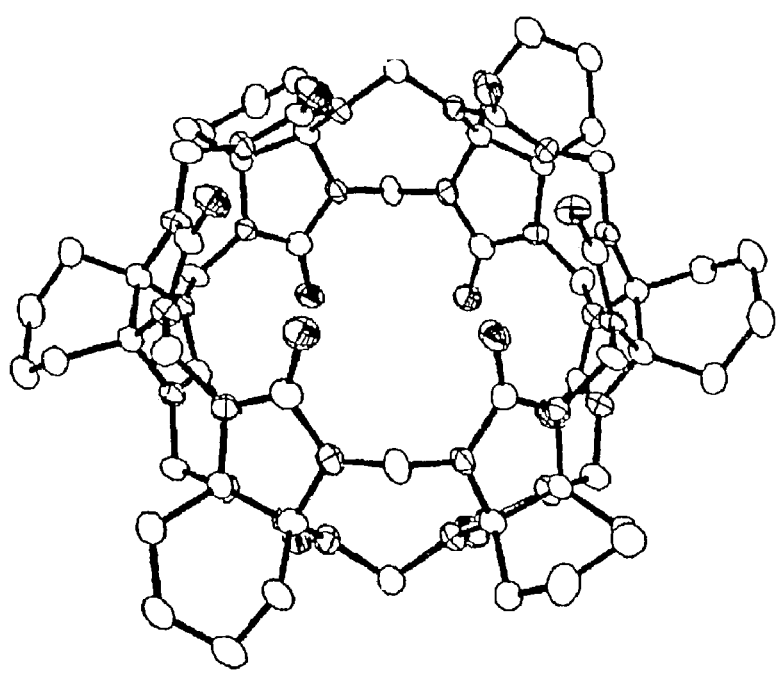
FIG. 2 is a diagram illustrating the X-ray crystal structures of cucurbituril derivatives prepared in Synthesis Example 2 of the present invention.

The crystal structure of the obtained cucurbituril derivative was determined by X-ray crystallography. The result is shown in FIG. 2. As shown in FIG. 2, it was confirmed that the cucurbituril derivative obtained in Synthesis Example 2 had internal cavities.

$^1$H NMR (300 MHz, $D_2O$): δ=5.73 (d, J=15.9 Hz, 12H), 4.32 (d, J=16.0 Hz, 12H), 2.26 (s, 24H), 1.49 (s, 24H); $^{13}$C NMR (75 MHz, $D_2O$): δ=156.43, 76.51, 44.10, 23.37, 14.07.

SYNTHESIS EXAMPLE 3

Preparation of the Glycoluril Derivative Having the Formula (2) where m=3, X=O, $R_1=H$ 2.0 g of 1 2-cyclopentanedione, 2.9 g of urea, 4 ml of trifluoroacetic acid were dissolved in 60 ml of benzene and refluxed at 80 to 90° C. for 16 hours. The water generated during the reaction was removed using a Dean-Stark water trap to promote the reaction. The resulting mixture was cooled to room temperature to generate the precipitate which was filtered and dried to give a solid glycoluril derivative where m=4, X=O and $R_1=H$ in 12% yield.

$^1$H NMR (300 MHz, DMSO-$d_6$): δ=7.25 (s, 4H), 1.90 (t, 4H), 1.67(m, 2H), $^{13}$C NMR (75 MHz, DMSO-$d_6$): δ=160.49, 81.70, 40,75, 23.55. MS (ESI): m/z 182.02

SYNTHESIS EXAMPLE 4

The desired product was synthesized by the same method as in Synthesis Example 1, except that a glycoluril derivative with m=1, X=S and $R_1=R_2=H$ and was used instead of the glycoluril derivative with m=4, X=O and $R_1=R_2=H$.

SYNTHESIS EXAMPLE 5

The desired product was synthesized by the same method as in Synthesis Example 1, except that a glycoluril derivative with m=2, X=O and $R_1=R_2=H$ and was used instead of the glycoluril derivative with m=4, X=O and $R_1=R_2=H$.

SYNTHESIS EXAMPLE 6

The desired product was synthesized by the same method as in Synthesis Example 1, except that a glycoluril derivative with m=3, X=O and $R_1=R_2=H$ and was used instead of the glycoluril derivative with m=4, X=O and $R_1=R_2=H$.

SYNTHESIS EXAMPLE 7

The desired product was synthesized by the same method as in Synthesis Example 1, except that a glycoluril derivative with m=5, X=O and $R_1=R_2=H$ and was used instead of the glycoluril derivative with m=4, X=O and $R_1=R_2=H$.

SYNTHESIS EXAMPLE 8

The desired product was synthesized by the same method as in Synthesis Example 1, except that a glycoluril derivative with m=7, X=O and $R_1=R_2=H$ and was used instead of the glycoluril derivative with m=4, X=O and $R_1=R_2=H$.

By similar methods to Synthesis Examples 1 through 8, the cucurbituril derivatives were obtained, where m=4, n=7, X=O, $R_1=R_2=H$; m=4, n=8, X=O, $R_1=R_2=H$; m=4, n=9, X=O, $R_1=R_2=H$; m=4, n=10, X=O, $R_1=R_2=H$; and m=4, n=4, X=O, $R_1=R_2=H$.

Also, by similar methods to Synthesis Examples 1 through 8, the cucurbituril derivatives were obtained, where m=3, n=7, X=O, $R_1=R_2=H$; m=3, n=8, X=O, $R_1=R_2=H$; m=3, n=9, X=O, $R_1=R_2=H$; m=3, n=10, X=O, $R_1=R_2=H$; and m=3, n=4, X=O, $R_1=R_2=H$.

SYNTHESIS EXAMPLE 9

The desired product was synthesized by the same method as in Synthesis Example 1, except that a compound (A) with m=4, X=S and $R_1=R_2=H$ and was used instead of the compound (A) with m=4, X=O and $R_1=R_2=H$.

SYNTHESIS EXAMPLE 10

The desired product was synthesized by the same method as in Synthesis Example 1, except that a compound (A) with m=4, X=NH and $R_1=R_2=H$ and was used instead of the compound (A) with m=4, X=O and $R_1=R_2=H$. By similar methods to Synthesis Examples 9 and 10, the cucurbituril derivatives were obtained, where n=5, m=3, X=S, $R_1=R_2=H$; n=6, m=3, X=S, $R_1=R_2=H$; n=7, m=3, X=S, $R_1=R_2=H$; n=8, m=3, X=S, $R_1=R_2=H$; n=5, m=4, X=S, $R_1=R_2=H$; n=6, m=4, X=S, $R_1=R_2=H$; n=7, m=4, X=S, $R_1=R_2=H$; n=8, m=4, X=S, $R_1=R_2=H$; n=5, m=3, X=NH, $R_1=R_2=H$; n=6, m=3, X=NH, $R_1=R_2=H$; n=7, m=3, X=NH, $R_1=R_2=H$; n=8, m=3, X=NH, $R_1=R_2=H$; n=5, m=4, X=NH, $R_1=R_2=H$; n=6, m=4, X=NH, $R_1=R_2=H$; n=7, m=4, X=NH, $R_1=R_2=H$; and n=8, m=4, X=NH, $R_1=R_2=H$.

SYNTHESIS EXAMPLE 11

Preparation of the Glycoluril Derivative Having the Formula (2) where m=4, X=O, $R_1=H$ 5.0 g of 1,2-cyclohexanedione, 6.7 g of urea, 10 ml of trifluoroacetic acid were dissolved in 170 ml of benzene and refluxed at 80 to 90° C. for 18 hours. The water generated during the reaction was removed using a Dean-Stark water trap to promote the reaction. The resulting mixture was cooled to room temperature to generate the precipitate which was filtered and dried to give a solid glycoluril derivative where m=4, X=O and $R_1=R_2=H$ in 71% yield.

$^1$H NMR (300 MHz, DMSO-$d_6$): δ=7.03 (s, 4H), 1.69 (t, 4H), 1.39(t, 4H); $^{13}$C NMR (75 MHz, DMSO-$d_6$): δ=161.19, 74.52, 32.37, 18.43. MS (EI): m/z 196.00.

SYNTHESIS EXAMPLE 12

The glycoluril derivative having the formula (2) with m=5, X=O and $R_1=H$ was synthesized by the similar method as in Synthesis Example 3.

SYNTHESIS EXAMPLE 13

The glycoluril derivatives having the formula (2) with m=3, X=S and $R_1=H$; and m=4, X=S and $R_1=H$ were synthesized by the similar method as in Synthesis Example 3.

SYNTHESIS EXAMPLE 14

The glycoluril derivatives having the formula (2) with m=3, X=NH and $R_1=H$; and m=4, X=NH and $R_1=H$ were synthesized by the similar method as in Synthesis Example 3.

Solubilities of the cucurbituril derivatives synthesized in Examples 1 and 2 were measured in water, methanol, dimethylsulfoxide and acetonitrile, and the result is shown in Table 1.

TABLE 1

| Solvent | CB*[5] | CB*[6] |
| --- | --- | --- |
| Water | $2.6 \times 10^{-1}$M | $1.7 \times 10^{-1}$M |
| Methanol | $3.1 \times 10^{-2}$M | $4.3 \times 10^{-1}$M |
| Dimethylsulfoxide | $1.8 \times 10^{-2}$M | $3.9 \times 10^{-1}$M |
| Acetonitrile | $6.7 \times 10^{-4}$M | $2.1 \times 10^{-1}$M |

As shown in Table 1, the cucurbituril derivatives obtained in Synthesis Examples 1 and 2 have good solubility in water at a neutral pH and organic solvents and have internal cavities, which was confirmed by X-ray crystal structure determination. Thus, inclusion complexes with organic compounds can be effectively produced, which has been verified in the following examples.

EXAMPLE 1

6.6 mg of CB*[6] synthesized in Synthesis Example 2 and 10 ml tetrahydrofuran were dissolved in 0.5 ml of $D_2O$. NMR spectroscopy confirms quantitative formation of a 1:1 host-guest complex.

$^1$H NMR (D$_2$O, 500 MHz): δ=5.72 (d, 12H), 4.26 (d, 12H), 2.86 (m, 4H), 2. 23 (s, 24H), 1.46 (s, 24H), 1.01 (m, 4H)

EXAMPLE 2

6.6 mg of CB*[6] synthesized in Synthesis Example 2 and 10 ml of cyclopentane were dissolved in 0.5 ml of D$_2$O. NMR spectroscopy confirms quantitative formation of a 1:1 host-guest complex.

$^1$H NMR (D$_2$O, 500 MHz): δ=5.77 (d, J=15.0 Hz, 12H), 4.22 (d, J=16.0 Hz, 12H), 2.23 (s, 24H), 1.45 (s, 24H), 0.70 (s, 10H).

EXAMPLE 3

6.6 mg of CB*[6] synthesized in Synthesis Example 2 and 1.2 mg of paratoluidine were dissolved in 0.5 ml of D$_2$O. NMR spectroscopy confirms quantitative formation of a 1:1 host-guest complex.

$^1$H NMR (D$_2$O, 500 MHz): δ=6.63 (d, 2H), 6.52 (d, 2H), 5.73 (dd, 12H), 4. 19 (dd, 12H), 2.25 (s, 24H), 2.11 (s, 3H), 1.45 (s, 24H).

EXAMPLE 4

6.6 mg of CB*[6] synthesized in Synthesis Example 2 and 1.5 mg of paratoluidine hydrochloride were dissolved in 0.5 ml of D$_2$O. NMR spectroscopy confirms quantitative formation of a 1:1 host-guest complex.

$^1$H NMR (D$_2$O, 500 MHz): δ=6.65 (d, 2H), 6.53 (d, 2H), 5.73 (dd, 12H), 4. 19 (t, 12H), 2.20 (s, 24H), 2.05 (s, 3H), 1.46 (s, 24H).

EXAMPLE 5

6.6 mg of CB*[6] synthesized in Synthesis Example 2 and 1.2 mg of 1,4-phenyline diamine were dissolved in 0.5 ml of D$_2$O. NMR spectroscopy confirms quantitative formation of a 1:1 host-guest complex.

$^1$H NMR (D$_2$O, 500 MHz): δ=6.21 (d, 4H), 5.79 (d, 12H), 4.26 (d, 12H), 2. 26 (s, 24H), 1.51 (s, 24H).

The above results of Examples 1 through 5 show that the cucurbituril derivatives obtained in Synthesis Examples 1 and 2 are advantageously used in extraction, separation and purification of the organic materials used in the examples.

The cucurbituril derivative obtained in Synthesis Example 2 is capable of forming a gaseous inclusion complex in its cavities, which has been verified in Example 6.

EXAMPLE 6

6.6 mg of CB*[6] synthesized in Synthesis Example 2 was dissolved in 0.5 ml of D$_2$O and isobutene gas was inspired into the resultant product for 10 minutes. NMR spectroscopy confirms quantitative formation of a 1:1 host-guest complex.

$^1$H NMR (D$_2$O, 500 MHz): δ=5.77 (d, 12H), 4.26 (d, 12H), 3.90 (s, 2H), 2.26 (s, 24H), 1.50 (s, 24H), 1.00 (s, 6H).

The result of Example 6 shows that the cucurbituril derivative obtained in Synthesis Example 2 can be advantageously used in extraction, separation and purification of the gaseous molecules used in the examples, and detection of other contaminants in the air.

The following example is for investigating whether the cucurbituril derivatives can effectively transport physiologically active materials or drugs. In the example, acetylcholine chloride, a neurotransmitter, was used.

EXAMPLE 7

6.6 mg of CB*[6] synthesized in Synthesis Example 2 and 2.0 mg of acetylcholine chloride were dissolved in 0.5 ml of D$_2$O. NMR spectroscopy confirms quantitative formation of a 1:1 host-guest complex.

$^1$H NMR (D$_2$O, 500 MHz): δ=5.81 (dd, 12H), 4.27 (dd, 12H), 3.99 (s, 2H), 3.8 (s, 2H), 3.36 (s, 9H), 2.27 (s, 24H), 1.46 (s, 24H), 1.15 (s, 3H).

On the other hand, the cucurbituril derivative obtained in Synthesis Example 1 has Lewis base atoms near the cavities of the molecule, and thus they can effectively form a complex with positively charged metal ions or other organic ions. The following example is for investigating whether the cucurbituril derivatives having this property can be applied in manufacturing sensors for sensing positive metal ions or ammonium ions.

EXAMPLE 8

A 5.5 mM CB*[5] solution and 110 mM-KCl solution were prepared with 0.05 M tris buffered solution having a pH of 7.2. Then, the binding constant of CB*[5] was measured using a microcalorimeter (VP-ITC, manufactured by MicroCal). As a result, CB*[5] forms a 1:2 complex with potassium ions with a primary binding constant of $2.8 \times 10^4$ M$^{-1}$ and a secondary binding constant of $1.5 \times 10^2$ M$^{-1}$. CB*[5] can selectively bind with alkali metal ions, as well as with ammonium ions. The result confirms that cucurbituril derivatives can be used as ion sensors.

The following example is for investigating whether ammonium ions present in an organic solvent can bind with CB*[5].

EXAMPLE 9

5.5 mg of CB*[5] synthesized in Synthesis Example 1 and 6.7 mg of (NH$_4$)$^+$(BPh$_4$)$^{31}$ were dissolved in 0.5 ml of CD$_3$CN. NMR spectroscopy confirms binding of ammonium ions of (NH$_4$)$^+$(BPh$_4$)$^-$ with CB*[5] at an equivalent ratio of 2:1.

$^1$H NMR (CD$_3$CN, 500 MHz):δ=7.24 (s, 16H), 6.99 (t, 16H), 6.84 (t, 8H), 6.21 (brs, 8H), 5.55 (d, 10H), 4.09 (d, 10H), 2.04 (s, 20H), 1.36 (s, 20H).

The following example is for investigating selectivity to detrimental heavy metal ions such as lead ions using an ion selective electrode having an ion selective membrane by a preparation method of the ion selective electrode using CB*[5] prepared in Synthesis Example 1.

EXAMPLE 10

A solution obtained by dissolving 1 wt % of CB*[5] prepared in Synthesis Example 1 in 0.1 mL of methanol and a 0.4 mL tetrahydrofuran solution obtained by dissolving 33 wt % of polyvinylchloride, a polymer support, 65.6 wt % of 2-nitrophenyloctylether, a plasticizer, and 0.4 wt % of potassium tetrakis(4-chlorophenyl)borate, were homogenously mixed and a solvent was then removed slowly to form an ion selective membrane. An ion selective electrode was manufactured using the ion selective membrane. Here, a silver chloride coated Ag wire immersed in 0.05 M KCl aqueous solution was used as a reference electrode.

The reference electrode and the ion selective electrode were immersed in 250 mL of a 1 mM $Mg(OAc)_2$-HCl buffered solution having a pH of 4 and the resultant product was kept stirring at least one hour until the layer exhibited a stable boundary potential. Thereafter, potential differences were measured while increasing the concentration of lead ions by 10 folds from $10^{-6}$ M to $10^{-3}$ M using a micro pipet at intervals of 100 seconds. Selectivities to lead ions were measured by a fixed solution method at a concentration of 0.01 M. The measurement result is given in FIG. 3 and Table 2.

Figure 3:
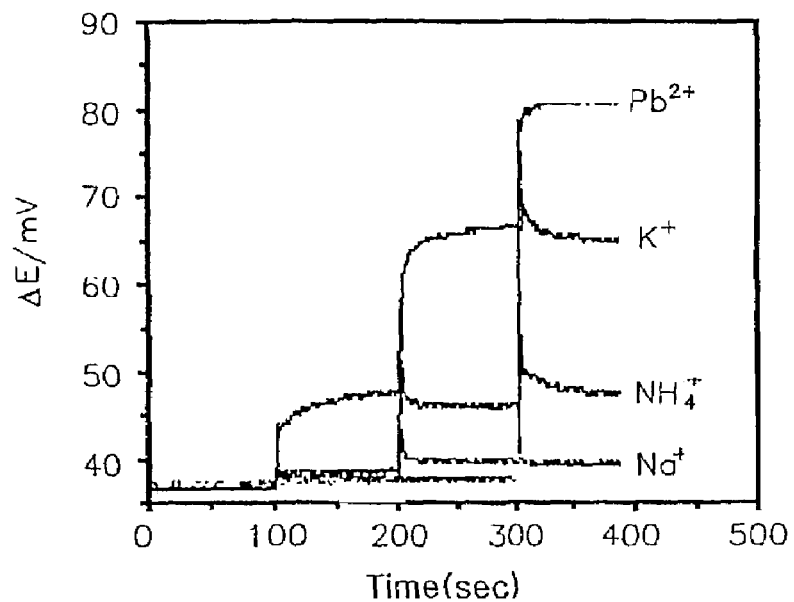
FIG. 3 is a graphical representation of lead ions, potassium ions, ammonium ions and sodium ions sensed from an ion selective electrode prepared using a cucurbituril derivative CB*[5] prepared in Synthesis Example 1 of the present invention.

FIG. 3 is a graphical representation of lead ions, potassium ions, ammonium ions and sodium ions sensed from an ion selective electrode prepared using a cucurbituril derivative CB*[5] prepared in Synthesis Example 1 of the present invention, and Table 2 shows selectivities for these ions.

TABLE 2

| Ions analyzed | Selectivity (log $K_{Pb2+}$) | Detection limit (mol/L) |
| --- | --- | --- |
| $Pb^{2+}$ | 0 | $2.5 \times 10^{-7}$ |
| $K^+$ | −1.2 | $6.0 \times 10^{-5}$ |
| $NH_4^+$ | −1.8 | $4.0 \times 10^{-4}$ |
| $Na^+$ | −2.3 | $5.3 \times 10^{-4}$ |

The results shown in FIG. 3 and Table 2 show that the ion selective electrode manufactured using CB*[5] prepared in Synthesis Example 1 can be used to detect detrimental heavy metal ions such as lead ions or mercury ions remaining in water.

The following example is for investigating selectivity to acetylcholine, a neurotransmitter, using an ion selective electrode having an ion selective membrane by a preparation method of the ion selective electrode using CB*[6] prepared in Example 1.

EXAMPLE 11

A solution obtained by dissolving 1 g of CB*[6] prepared in Example 1 in 0.1 mL of methanol and a 0.4 mL tetrahydrofuran solution obtained by dissolving 33 g of polyvinylchloride, a polymer support, 65.6 g of 2-nitrophenyloctylether, a plasticizer, and 0.4 g of potassium tetrakis(4-chlorophenyl)borate, were homogenously mixed and a solvent was then removed slowly to form an ion selective membrane. An ion selective electrode was manufactured using the ion selective membrane. Here, a silver chloride coated Ag wire immersed in 0.05 M KCl aqueous solution was used as a reference electrode.

The reference electrode and the ion selective electrode were immersed in 250 mL of a 0.05 M Tris-HCl buffered solution having a pH of 7.2 and the resultant product was kept stirring at least one hour until the layer exhibited a stable boundary potential. Thereafter, potential differences were measured while increasing the concentration of lead ions by 10 folds from $10^{-6}$ M to $10^{-1}$ M using a micro pipet at intervals of 100 seconds. Selectivities to lead ions were measured by a fixed solution method at a concentration of 0.01 M. The measurement result is given in FIG. 4 and Table 3.

Figure 4:
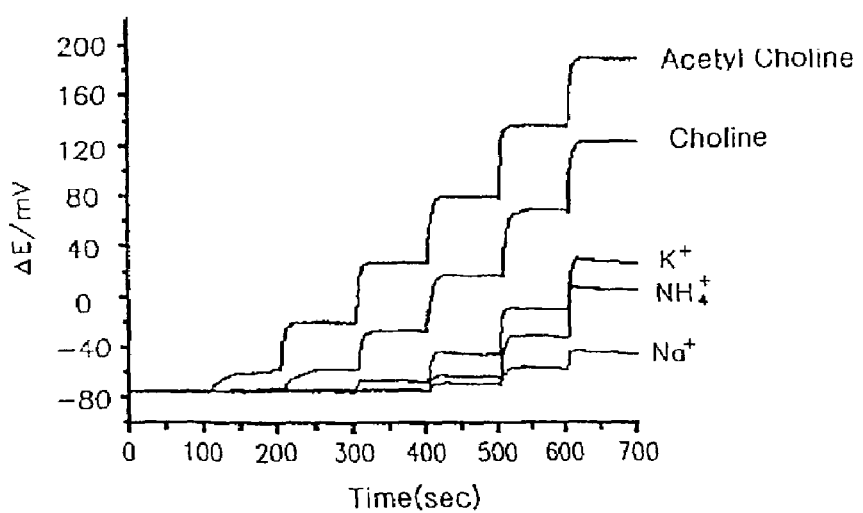
FIG. 4 is a graphical representation of lead ions, potassium ions, ammonium ions and sodium ions sensed from an ion selective electrode prepared using a cucurbituril derivative CB*[6] prepared in Synthesis Example 2 of the present invention.

FIG. 4 is a graphical representation of lead ions, potassium ions, ammonium ions and sodium ions sensed from an ion selective electrode prepared using a cucurbituril derivative CB*[6] prepared in Example 1 of the present invention, and Table 3 shows selectivities-for these ions.

TABLE 3

| Ions analyzed | Selectivity (log $K_{Acetylcholine}$) | Detection limit (mol/L) |
| --- | --- | --- |
| Acetylcholine | 0 | $6.3 \times 10^{-7}$ |
| Choline | −1.2 | $8.3 \times 10^{-11}$ |
| $K^+$ | −2.7 | $6.9 \times 10^{-5}$ |
| $NH_4^+$ | −3.1 | $5.2 \times 10^{-4}$ |
| $Na^+$ | −3.9 | $3.2 \times 10^{-4}$ |

The results shown by Example 11 show that the ion selective electrode manufactured using CB*[6] prepared in Example 1 can selectively recognize a neurotransmitter in vivo, e.g., acetylcholine, to be used for clinical analysis.

As described above, since the cucurbituril derivatives having the formula (1) according to the present invention, are soluble in water at a neutral pH or in methanol, a common organic solvent, they have wider applications than conventional cucurbituril derivatives. Also, the cucurbituril derivatives can encapsulate various compounds with different sizes, and have Lewis base atoms near the entrances to their cavities so that they can form complexes with metal ions, organometallic ions or positively charged organic compounds. With these features, the cucurbituril derivatives according to the present invention have very wide applications. In addition, the preparation of the cucurbituril derivatives according to the present invention is easily scaled up for industrial purposes. In the cucurbituril derivative preparation according to the present invention, each cucurbituril derivative can be separated from the mixture containing the cucurbituril derivatives having the formula (1), where n is a value from 4 to 20, and a mixture of two or more of the cucurbituril derivatives can also be obtained.

The cucurbituril derivatives and the mixture thereof disclosed by the present invention are applied to remove organic dyes from waste water, heavy metal from water and radioactive isotopes from radioactive wastes, to capture and remove unpleasant odor, and air pollutants such as carbon monoxide, carbon dioxide, $NO_x$ and $SO_x$, and to deodorize and decolorize livestock waste water and ironwork waste water. Also, the cucurbituril derivatives disclosed by the present invention are applicable in manufacturing sensors for sensing ammonium ions, organic amines, amino acid derivatives, nucleic acid bases, alkali metal or alkaline earth metal ions. The cucurbituril derivatives can be used as additives to polymers, cosmetics, artificially scented papers or textiles, pesticides, drugs and foods, and used as drug carriers. The cucurbituril derivatives having the formula (1) can be used for extraction and purification of fullerene or caborane compounds, and used as packing materials of chromatographic columns, as additives to gas separation membranes, as catalysts for various chemical reactions. In particular, since the cucurbituril derivatives according to the present invention are soluble in water at a neutral pH, they can be advantageously used in recognizing physiologically active materials in vivo, e.g., acetylcholine. Also, since increased solubility of the cucurbituril derivatives in organic solvents makes it easy to manufacture ion selective electrode membranes, the cucurbituril derivatives can be used for development of ionic sensors directly applicable for clinical analysis or detection of environmental pollutants. In addition, use of the mixture of cucurbituril derivatives prepared by the method shown in FIG. 1 without separation is advantageous in terms of cost, and can be readily adapted for industrial uses.

Also, the glycoluril derivatives having the formula (2) can be advantageously used in preparing the cucurbituril derivatives having the formula (1).

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cucurbituril derivative having the formula (1):

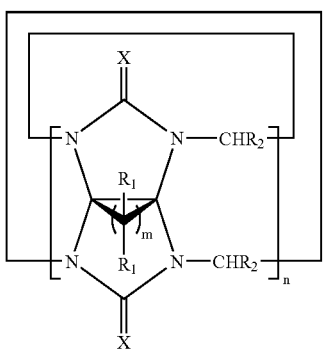

(1)

where X is O, S or NH; $R_1$ and $R_2$ are methyl; and n and m are independently integers from 4 to 10 and from 1 to 7, respectively.

2. The cucurbituril derivative according to claim 1, wherein X=O and n is a value of 4 to 10 and m is a value of 1 to 7.

3. The cucurbituril derivative according to claim 1, wherein X=NH or S and n is a value of 4 to 10 and m is a value 1 of 7.

4. A method for preparing a cucurbituril derivative having the formula (1), comprising:

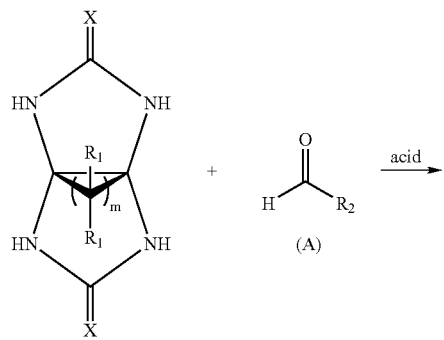

-continued

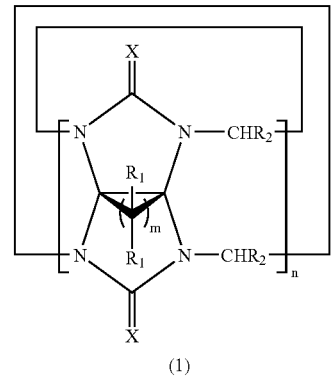

(1)

(a-2) mixing and stirring a compound having the formula (2) and an aldehyde compound having the formula (A); and (b-2) adding acid to the reaction mixture and stirring to complete the reaction, where X is O, S or NH; $R_1$ and $R_2$ are methyl; and n and in are independently integers from 4 to 10 and from 1 to 7, respectively.

5. The method according to claim 4, wherein in step (a-2), the acid is added in an amount of 3 to 7 moles and the aldehyde compound having the formula (A) is added in an amount of 2 to 20 moles with respect to 1 mole of the compound having the formula (2), and the reaction temperature is in the range of 50 to 150° C.

6. The method according to claim 4, wherein in step (b-2), the reaction temperature is in the range of 50 to 150° C.

7. The method according to claim 4, wherein in step (a-2), the acid is selected from the group consisting of hydrochloric acid, sulfuric acid, phosphoric acid, acetic acid and nitric acid and is used as a diluted solution in water or an organic solvent.

8. The method according to claim 4, wherein among reaction products of step (b-2), the cucurbituril derivative with n=5 is produced in a yield of 15 to 50%, the cucurbituril derivative with n=6 is produced in a yield of 2 to 10%, and the cucurbituril derivatives with n=4 and 7 to 10 are produced in a yield of 1 to 5%, respectively.

9. A The method according to claim 4, further comprising separating the cucurbituril derivative having the formula (1) from the cucurbituril derivative mixture by fractional crystallization.

10. The method according to claim 9, wherein at least one solvent selected from the group consisting of water, acetone and acetonitrile is used in the fractional crystallization.

* * * * *